United States Patent [19]

Rauch et al.

[11] Patent Number: 4,592,080
[45] Date of Patent: May 27, 1986

[54] COMPUTER TOMOGRAPH

[75] Inventors: Werner Rauch, Nuernberg; Guenter Schmitt, Erlangen; Edgar Tschunt, Rathsberg, all of Fed. Rep. of Germany

[73] Assignee: Siemens Aktiengesellschaft, Berlin & Munich, Fed. Rep. of Germany

[21] Appl. No.: 613,386

[22] Filed: May 23, 1984

[30] Foreign Application Priority Data

Jul. 29, 1983 [DE] Fed. Rep. of Germany ....... 3327707

[51] Int. Cl.⁴ ............................................ G01N 23/00
[52] U.S. Cl. ......................................... 378/19; 378/10
[58] Field of Search ................................... 378/10, 19

[56] References Cited

U.S. PATENT DOCUMENTS 4,153,842  5/1979  Rohmfeld .
4,219,733  8/1980  Tschunt .
4,227,088 10/1980  Maydan ................................. 378/10
4,246,484  1/1981  Fetter ................................... 378/10

Primary Examiner—Craig E. Church
Attorney, Agent, or Firm—Hill, Van Santen, Steadman & Simpson

[57] ABSTRACT

An annular radiation receiver consisting of individual detectors, is stationary, and an X-ray source is rotated along a path surrounding the detectors. The individual detectors of the radiation receiver are combined into detector groups having an equal number of individual detectors, and the detector groups are adjustable independently of one another in such a fashion that those individual detectors which are disposed in advance of the radiography subject are respectively moved out of the X-ray beam. To this end, a cam plate can be present which is rotatable synchronously with the rotation of the X-ray beam, to which levers are coupled which control the detector groups.

1 Claim, 2 Drawing Figures

COMPUTER TOMOGRAPH

BACKGROUND OF THE INVENTION

The invention relates to a computer tomograph including a measuring unit comprised of an X-ray source and a radiation receiver, in which the X-ray source emits a fan-shaped X-ray beam which strikes an annular radiation received formed of a series of individual detectors, each of which supplies an electric signal corresponding to the received radiation intensity, in which means are provided for the rotation of the X-ray beam about the radiography subject for the purpose of irradiation of a layer of the radiography subject, lying in the fan plane, from various directions, in which a measured valued processing unit is present to which the output signals of the individual detectors for the various irradiation directions are supplied, and which measurand processing unit determines therefrom the attenuation values of predetermined points in the irradiated plane of the radiography subject, and in which an image display device is present for the image-display of the calculated attenuation values, wherein each individual detector is adjustable in such a fashion that it can be brought from a position outside the X-ray beam into a position in which it is impinged upon by the X-ray beam.

In the case of a known computer tomograph of this type, the radiation receiver is mounted on gimbals and that portion of the receiver which is required for the purpose of detection of the X-radiation issuing from the radiography subject is respectively pivoted into the X-ray beam with the aid of guide means. A swiveling motion of the radiation receiver thereby results, and the individual detectors are not respectively perpendicularly impinged upon by X-radiation. In addition, the moved masses are relatively large, which is particularly disadvantageous when short scanning times are desired for which a rapid swiveling motion is required.

In a further known computer tomograph of the initially cited type, each individual detector is adjustably mounted so that it can be selectively moved into the X-ray beam or out of the latter. Indeed, a motion of the entire radiation receiver is thereby avoided; however, the constructional outlay for the adjustment of the individual detectors is very great.

SUMMARY OF THE INVENTION

The object underlying the invention resides in designing a computer tomograph of the initially cited type in such a fashion that, with a reduced structural outlay as compared with the state of the art, pursuant to avoidance of a swiveling motion of the radiation receiver, that part of the radiation receiver which is disposed in advance of the radiography subject—viewed in the radiation direction—is removed from the X-radiation in a simple fashion.

This objective is achieved in accordance with the invention in that the individual detectors are combined into detector groups with the same number of individual detectors, and that the detector groups are adjustable independently of one another. In the inventive computer tomograph, those detector groups which—viewed in the radiation direction—are disposed in advance of the radiography subject are so adjusted that they do not interfere with the X-radiation. The groupwise adjustment requires a relatively low structural outlay.

A particularly expedient solution for the adjustment of the detector groups is one where a cam plate, which is synchronously rotatable with the rotation of the X-ray beam, is present, to which levers are coupled which act upon the detector groups. These levers can be under spring action so that, with one end, they are respectively pressed against the cam plate and are moved corresponding to an actuating cam contour of the cam plate. The control of the detector groups can proceed in an impositive manner (e.g. with spring means effecting the desired positioning) or in a positive manner (connecting link or doubled cam positively establishing the detector positions).

The invention shall be explained in greater detail in the following on the basis of an exemplary embodiment illustrated on the accompanying drawing sheet; and other objects, features and advantages will be apparent from this detailed disclosure and from the appended claims.

DETAILED DESCRIPTION

Figure 1:
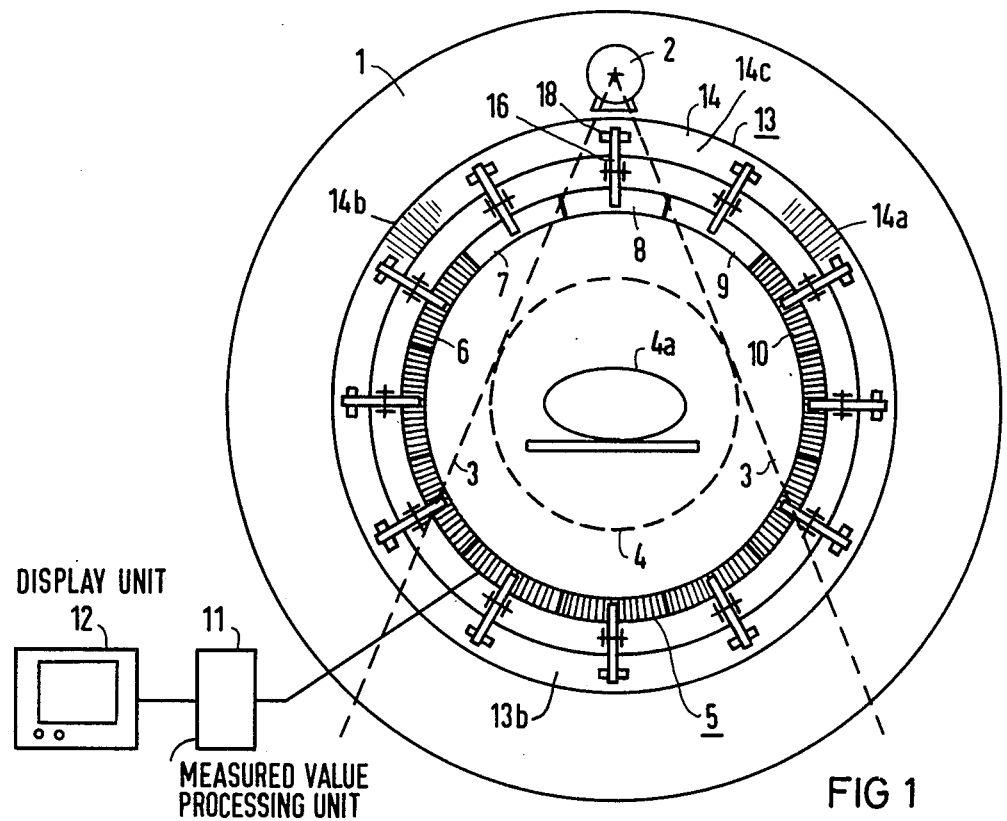
FIG. 1 is a diagrammatic view showing the significant parts of a computer tomograph according to the invention.

FIG. 1 shows a rotatable ring 1 to which an X-ray source 2 is fixedly secured. The X-ray source 2 emits a fan-shaped X-ray beam 3 whose marginal rays are tangential to a circular measuring field 4 during rotation of the ring 1. The measuring unit of the illustrated computer tomograph contains, in addition to the X-ray source 2, a radiation receiver 5 which is comprised of a series of individual detectors which surround the measuring field in an annular fashion. The individual detectors of the radiation receiver 5 are combined into successive detector groups 6, 7, 8, 9, 10, etc., each group having the same number of detectors. The detector groups such as 6 through 10 are adjustable individually, independently of one another, perpendicularly to the fan-plane of the X-ray beam 3 in the manner described in further detail in the following so that those detector groups, respectively, which are disposed—viewed in the radiation direction—in advance of the radiography subject 4a lying in the measuring field, can be moved out of the X-ray beam 3. The groups which have been moved out of the beam path for the illustrated position of the X-ray source 2, are the detector groups 7, 8 and 9. Accordingly, the X-ray beam 3 directly impinges on the radiography subject 4a without obstruction and, after its emergence from the radiography subject 4a, it strikes the individual detectors disposed in the path of the X-ray beam. These individual detectors, given the various irradiation directions which are obtained through rotation of the X-ray source 2 on the rotating ring 1, deliver electric signals which correspond to the respectively received radiation intensity, which electric signals are supplied to a measurand processing unit 11. The measurand processing unit 11 calculates from these signals the attenuation values of predetermined points in the irradiated plane of the radiography subject in the measuring field 4 and these attenuation values are displayed on a display unit 12 in the form of an image of the plane.

Figure 2:
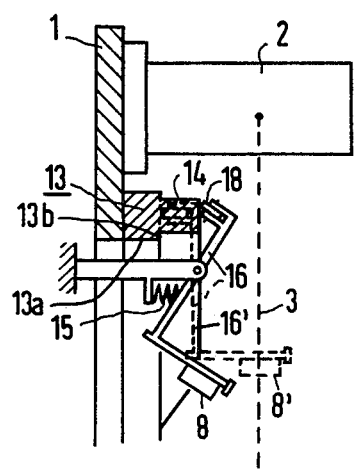
FIG. 2 is a partial sectional view showing a detail of the computer tomograph according to FIG. 1 as viewed in a circumferential direction.

For the adjustment of the detector groups 6 through 10, etc., there is provided on the rotating ring 1 a cam plate 13 which has a raised portion 14. The portion 14 provides a shock-free and jolt-free cam for effecting movement of the detector groups according to a sinusoidal function. Levers are pressed with their one ends against the cam plate 13, with the aid of compression springs, of which one is visible in FIG. 2 and referenced with 15, which levers, at their other ends, respectively, support a detector group such as 6 to 10, etc. In FIG. 2, the detector group 8 and the lever 16 for this detector group 8 are illustrated. For detection of the X-radiation the detector groups such as 6 through 10 assume the position illustrated in broken lines at 8' in FIG. 2 for the detector group 8. If one of the detector groups, in the example, the detector groups 7 through 9, of which only the detector group 8 is visible in FIG. 2, is to be pivoted out of the X-ray beam 3, this proceeds via the ascent of a roller 18 at the end of the respective lever 16 on the portion 14 of the cam plate 13.

The detector groups 6 through 10, etc., and the respective levers, accordingly, in this instance, then assume the position illustrated in broken lines in FIG. 2 for the components 8', 16'.

The exemplary embodiment shows that through a minimum constructive outlay a reliable and rapid pivoting-out of individual detectors from the X-ray beam 3 takes place so that the detectors which would obstruct the free access of the X-ray beam 3 to the measuring field and to a radiography subject therein are shifted to a beam clearance position. Accordingly, the invention relates to a computer tomograph comprising a detector ring and an X-ray source outside said detector ring which is rotated about the latter.

It will be apparent that many modifications and variations may be made without departing from the scope of the teachings and concepts of the present invention.

SUPPLEMENTARY DISCUSSION

In the exemplary embodiment the cam plate may comprise a base portion 13a of rectangular cross section, FIG. 2, which is fixedly secured to rotary frame 1. As indicated in dash outline in FIG. 2, in the operative region of the detector array the rollers 18 of the levers 16 ride on an annular face 13b of of the base portion 13a, such that the springs 15 hold the active detector groups in the plane of fan beam 3. As the cam plate 13 rotates with the rotary frame 1, a leading cam contour at 14a of cam portion 14 engages the roller 18 of the lever supporting detector group 10, for example, and this detector group is gradually shifted as a unit from a beam intercepting position such as indicated at 8' in FIG. 2, to the retracted position where the entire set of detectors is offset from the fan beam 3 as shown in solid lines at 8 in FIG. 2. The rate of movement of each detector group under the control of the sloping leading cam contour at 14a, FIG. 1, begins gradually, becomes more rapid and then gradually diminishes in accordance with a sinusoidal time function as frame 1 rotates at constant speed. The trailing cam contour at 14b is complementary to the leading cam contour 14a and allows the springs 15 to return the successive detector groups to the beam intercepting position in accordance with a corresponding sinusoidal function. In the illustrated embodiment, the rollers 18 are located at thirty degree intervals, and the constant level portion 14c of cam portion 14 extends over an angular extent greater than sixty degrees, so that a detector group such as 10, FIG. 1, has been fully retracted before the fan beam 3 approaches the vicinity of this detector group. Similarly, a detector group such as 7 returns to the operative position only after the beam has moved away from the vicinity of the group (where the frame 1 rotates clockwise from the position shown in FIG. 1).

We claim as our invention:

1. A computer tomograph comprising a measuring unit including an X-ray source and a radiation receiver, the X-ray source emitting a fan-shaped X-ray beam, the radiation receiver being of annular configuration and being formed of an array of individual detectors, each for supplying an electric signal corresponding to received radiation intensity, means for effecting the rotation of the X-ray beam about a radiography subject for the purpose of irradiation from various directions of a layer of the radiography subject, disposed in the plane of the fan-shaped X-ray beam, measured value processing circuitry for receiving the output signals of the individual detectors, which are obtained in the case of the various irradiation directions, and for determining attentuation values for predetermined points in the irradiated layer of the radiography subject, and an image display device for presenting an image display of the calculated attenuation values, each individual detector being mounted adjustably in such a fashion that it can be brought from a position outside the X-ray beam into a position in which it is impinged upon by the X-ray beam, characterized in that the individual detectors are combined into detector groups having an equal number of individual detectors, and that the detector groups are adjustable independently of one another, means for sequentially displacing detector groups adjacent said X-ray source out of said X-ray beam in synchronism with beam rotation characterized in that, for the adjustment of the detector groups a cam plate is present which is rotatable synchronously with the rotation of the X-ray beam, a plurality of pivoted levers with a lever connected to each detector group and engageable with the cam plate for controlling the adjustment of the respective detector groups during rotation of the X-ray beam to sequentially move them out of said X-ray beam in synchronism with rotation of said source and a plurality of springs attached to said plurality of levers to bias said levers to a position to move said detector groups into said X-ray beam.

* * * * *